(12) United States Patent
Takishita et al.

(10) Patent No.: US 8,881,731 B2
(45) Date of Patent: Nov. 11, 2014

(54) RESPIRATORY MASK SYSTEM

(75) Inventors: Masahide Takishita, Tokyo (JP);
Takamitsu Okayama, Tokyo (JP);
Keiko Omura, Tokyo (JP); Tongoh Chin, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1009 days.

(21) Appl. No.: 12/513,349

(22) PCT Filed: Oct. 18, 2007

(86) PCT No.: PCT/JP2007/070356
§ 371 (c)(1),
(2), (4) Date: May 1, 2009

(87) PCT Pub. No.: WO2008/053715
PCT Pub. Date: May 8, 2008

(65) Prior Publication Data
US 2010/0012128 A1    Jan. 21, 2010

(30) Foreign Application Priority Data

Nov. 2, 2006   (JP) ................................ 2006-298674

(51) Int. Cl.
*A61M 16/06* (2006.01)
*A61M 16/08* (2006.01)

(52) U.S. Cl.
CPC .......... *A61M 16/06* (2013.01); *A61M 16/0633* (2014.02); *A61M 16/0683* (2013.01); *A61M 16/0816* (2013.01); *A61M 16/0616* (2014.02)
USPC ............ 128/207.11; 128/206.21; 128/206.28; 128/205.25

(58) Field of Classification Search
USPC ............. 128/203.29, 204.11, 204.12, 205.25, 128/206.12, 206.13, 206.15, 206.16, 128/206.17, 206.21, 206.24, 206.28, 128/207.11, 207.13, 207.17, 207.18, 912; 285/51, 67, 74, 121.5; D29/108–112
See application file for complete search history.

(56) References Cited

U.S. PATENT DOCUMENTS 5,458,139 A * 10/1995 Pearl ........................ 128/207.14
5,572,994 A * 11/1996 Smith ....................... 128/207.18
5,662,101 A * 9/1997 Ogden et al. ............. 128/205.25

(Continued)

FOREIGN PATENT DOCUMENTS

JP    11-000397    1/1999
JP    11-397 A     6/1999

(Continued)

OTHER PUBLICATIONS

Taiwanese Office Action; Application No. 96139483; Nov. 21, 2012.

(Continued)

*Primary Examiner* — Tan-Uyen (Jackie) T Ho
*Assistant Examiner* — Peter S Vasat
(74) *Attorney, Agent, or Firm* — Sughrue Mion, PLLC (57) ABSTRACT

A respiratory mask system is provided, in which while wearing a respiratory mask system, force generated by movement of a user's head and the like to induce laterally slipping a mask cushion may be reduced or absorbed. The respiratory mask system is provided with a mask cushion covering a nose, a nose and a mouth, or a full face. A first frame is connected with the mask cushion to supply respiratory gas under positive pressure. A second frame is connected with a headgear strap, in which the mask cushion is placed on a face side of the first frame and the first frame is placed on a face side of the second frame. The first frame is connected slidably with the second frame along a slide surface.

8 Claims, 5 Drawing Sheets

(56) References Cited

U.S. PATENT DOCUMENTS

| | | | |
|---|---|---|---|
| 5,921,239 A * | 7/1999 | McCall et al. | 128/205.25 |
| 2002/0029780 A1 | 3/2002 | Frater et al. | |
| 2002/0078953 A1 | 6/2002 | Fecteau et al. | |
| 2006/0272646 A1 * | 12/2006 | Ho et al. | 128/207.11 |

FOREIGN PATENT DOCUMENTS

| | | |
|---|---|---|
| JP | 2002-537078 A | 11/2002 |
| JP | 2003-535657 A | 12/2003 |
| WO | 96/17643 A1 | 6/1996 |
| WO | 98/04310 A1 | 2/1998 |
| WO | 01/97893 A1 | 12/2001 |

OTHER PUBLICATIONS

Canadian Office Action issued Aug. 22, 2013 in corresponding Canadian Patent Application No. 2,667,889.

* cited by examiner

US 8,881,731 B2
RESPIRATORY MASK SYSTEM

TECHNICAL FIELD

The present invention relates to a respiratory mask system used for continuous positive airway pressure (CPAP) therapy suitable for the treatment of sleep apnea syndrome, nasal intermittent positive pressure ventilation (NIPPV) therapy suitable for ventilatory insufficiency, and the like.

BACKGROUND ART

One of the most effective therapeutic methods for sleep apnea syndrome is a continuous positive airway pressure (CPAP) method. While in this therapy a respiratory equipment is adopted for supplying positive pressure gas at about 400 to 2000 Pa to the nasal cavity, the nasal cavity and the mouth or the face of a user during sleep, in recent years devices with a function to control a pressure automatically responding to an occurrence state of apnea during therapy have also been used. A nasal intermittent positive pressure ventilation (NIPPV) method is used as one of the most effective therapeutic methods for ventilatory insufficiency, in which a respiratory equipment is adopted for supplying intermittent positive pressure gas at about 400 to 2400 Pa to the nasal cavity of a user. A mask for supplying positive pressure gas while applying pressure to the nasal cavity, a mask for supplying positive pressure gas while covering the nasal cavity and the mouth, and a mask for supplying positive pressure gas while covering the full face are called a nasal respiratory mask system, a full face mask, and a total face mask, respectively.

A nasal respiratory mask system is described as an example in the following, but its content may be applied to a general respiratory mask system including a full face mask, a total full face mask and the like.

Figure 1:
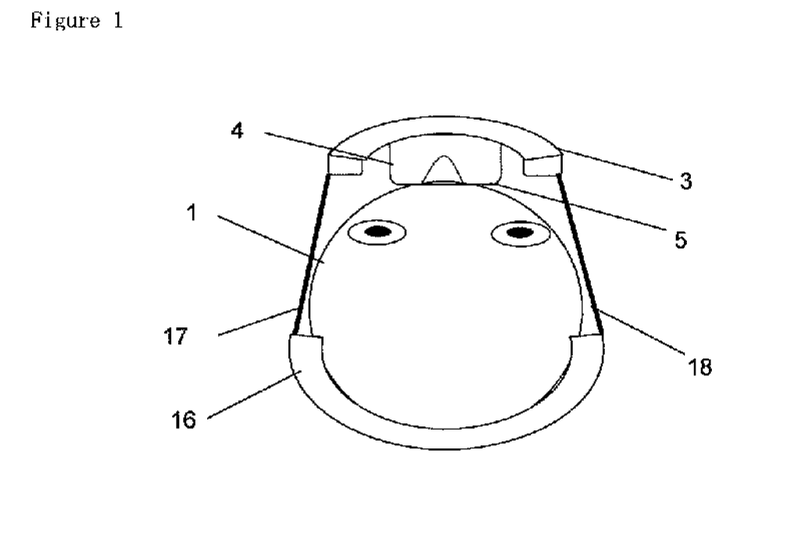
FIG. 1 is a schematic view of a conventional respiratory mask system.

A nasal respiratory mask system is, for example, as shown in FIG. 1, generally provided with a hollow nasal mask cushion 4 tightly sealing the face of a user, a frame 3 retaining the nasal mask cushion 4 at a predetermined position for supplying respiratory gas under positive pressure, a headgear 16 connected with this frame 3 and elastic headgear straps 17 and 18 to link this headgear 16 with the frame 3 in order to continuously supply positive pressure to the nasal cavity of a user (to both nose and mouth in case of a full face mask and to a full face in case of a total face mask). Such a nasal respiratory mask system then tightly seals the face of a user with the nasal mask cushion 4 by the tension of headgear straps 17 and 18 (see, for example, Patent Document 1, Patent Document 2 and Patent Document 3).

However, it is known that various factors cause slipping of the nasal mask cushion during wearing even if a nasal respiratory mask system is once worn properly. Accordingly, measures responding to each cause are taken to prevent or reduce its slip. For example, in a nasal respiratory mask system disclosed in Patent Documents 1 and 2, a bellow is mounted between a frame section and a face contact section of a nasal mask cushion to have no effect on the nasal mask cushion by slipping the frame section caused by contact with bedclothes. In a nasal respiratory mask system described in Patent Document 4, a flexible material is used in a wall around a connection section with a hose for supplying positive pressure gas in order to reduce slipping of a frame section pulled by the hose for positive pressure gas connected with the frame section.
Patent Document 1: Japan Patent Laid-Open Publication No. H11-000397.
Patent Document 2: WO 01/097893
Patent Document 3: WO 98/04310
Patent Document 4: WO 96/17643

DISCLOSURE OF INVENTION

Problems to be Solved by the Invention

However, it has been found that even if particular force is not applied from outside to a frame section and the like, for example, movement of user's head from side to side and up and down generates force to induce slipping of a nasal mask cushion section, resulting in its slipping state. Such slipping may not be eliminated immediately even after stopping head movement and often tends to stay without change.

For instance, when a user tilts his face to a right direction while in bed, such slipping is caused by tendency of a nasal respiratory mask system equipped with a nasal mask cushion and a frame to fall by its own weight in a lower right direction. Further tension is thus applied to the left side of a strap to press the left side of the cushion to a face, thus conversely loosening the right side of the strap. As a result, excess force is applied to the left side of the cushion to press a face generating pain, creating in the right side a gap between the face and the cushion to cause abnormal gas leak.

If such slip occurs but mild, a part of a contact surface of a nasal mask cushion with a face (for example, right side section) is stretched while the other part (for example, left side section) is shrunk, thus keeping a sort of a sealing state with a face. However, even if a sealing state is maintained, a user feels uncomfortable because of uneven pressure of a nasal mask cushion. That is, for example, when a user tilts his head to right in a state of being face up, a nasal respiratory mask system tends to slip to lower right by its own weight. A headgear to keep a frame at a predetermined position does not then move because of friction with a head, thereby applying tension to a left side strap and loosing a right side strap. This causes a tilt of a contact section of a mask cushion against a face, giving a user discomfort by uneven pressure of a nasal mask cushion.

Stretching of a contact surface of a face with a nasal mask cushion may not absorb such slip any more when such slip is further increased, resulting in leak of respiratory gas under positive pressure from a contact surface.

That is, an object of the present invention is to provide a nasal respiratory mask system capable of reducing or absorbing such lateral slip of a nasal mask cushion section unknown in the past. The present invention is effective to slipping by action of external force, but in particular, provides a nasal respiratory mask system with a mechanism to substantially prevent a mask cushion section from tilting to a face even if such slipping force is applied.

Means to Solve the Problems

The present invention is a nasal respiratory mask system contacting the face of a user for supplying respiratory gas under positive pressure to the user and provided with a mask cushion covering a nose, a nose and a mouth or a full face, a first frame connected with the above mask cushion and capable of supplying respiratory gas under positive pressure gas from a means for supplying respiratory gas under positive pressure, and a second frame connected with a headgear strap, in which the above mask cushion is disposed on a face side of the above first frame, the above first frame is disposed on a face side of the above second frame, a slide surface is formed on at least a side of the above first frame facing the above second frame and a side of the above second frame facing the above first frame, and the above first frame is connected slidably with the above second frame along the above slide surface.

A nasal respiratory mask of the present invention herein is mounted with a headgear strap on a second frame and a user wears the nasal respiratory mask system on his head with this headgear strap and a headgear. Positive pressure gas from a means for supplying respiratory gas under positive pressure is supplied via an elbow and the like to a first frame, thus supplying positive pressure gas to a user.

Figure 2:
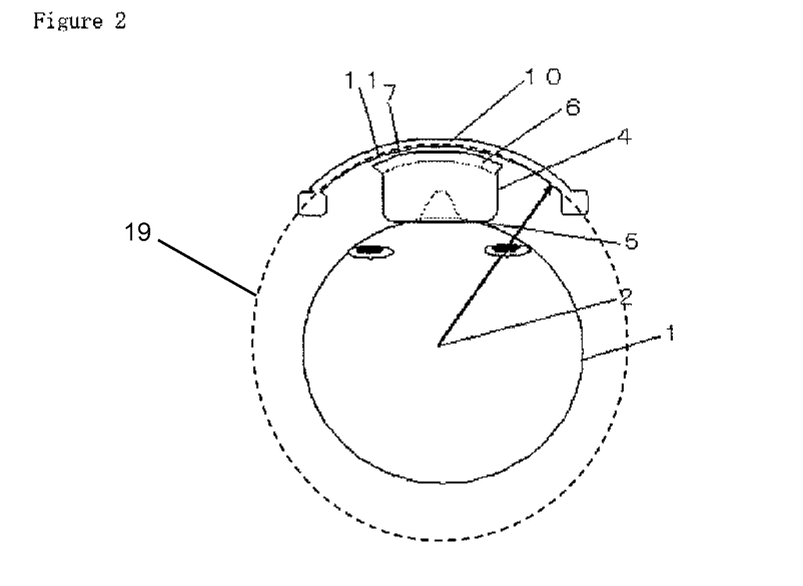
FIG. 2 is a schematic vies of a respiratory mask system of the present invention.

Such a basic principle of the present invention is described according to FIG. 2. In a nasal respiratory mask system of the present invention, a second frame 10 is fixed on the head 1 of a user via a headgear strap similarly as a frame 3 in a conventional nasal respiratory mask system shown in FIG. 1. On the other hand, since a first frame 6 is positioned closer to the face side than a second frame 10 and a mask cushion 4 is positioned further closer to the face side than the first frame 6, application of tension to a headgear strap enables the mask cushion 4 to seal the face of a user. When the head 1 of a user moves from side to side and up and down or external force is acted on the mask herein, the second frame 10 experiences force to be displaced relatively to the head 1 of a user in the nasal respiratory mask system of the present invention. However, since the first frame 6 is connected slidably with the second frame 10 along slide surfaces 7 and 11, problematic lateral slip may be reduced or absorbed by slide surfaces 7 and 11 even if force is applied in the direction of lateral slip of the first frame 6 and the second frame 10. In particular, when the slide surfaces 7 and 11 are formed in a spherical shape and a convex shape protruding in the opposite direction to a face side, and the first frame 6 is connected with the second frame 10 in a ball-joint like form through the slide surfaces 7 and 11, relative movement between the first frame 6 and the second frame 10 becomes smoother to further reduce or absorb the lateral slip. Furthermore, when the center of a spherical surface in these slide surfaces 7 and 11 is positioned above or near the center of the revolving movement of the head 1 of a user from side to side and up and down, tilting the head 1 of a user from side to side and up and down does not tilt the mask cushion 4 against the face of a user, thus keeping the pressure from the mask cushion to the face of a user to be uniform.

Effect of Invention

A nasal respiratory mask system of the present invention allows relative movement between a first frame and a second frame to reduce or absorb the lateral slip, even when force such as movement of the user's head and the like is applied in the direction to induce lateral slip of a mask cushion. Thus, by substantially preventing the mask cushion from tilting against a face, discomfort of a user is reduced and air tightness of the mask cushion to the face is maintained.

A nasal respiratory mask system of the present invention, for example, may also use a resin for a first frame and a second frame to make it thin and solve problematic slip by such a simple mechanism, forming a lightweight nasal respiratory system.

SYMBOLS IN DRAWINGS

1. Head of user
2. Center of slide surface of mask cushion
3. Frame in conventional product
4. Mask cushion
5. Face contact section of mask cushion
6. First frame
7. Slide surface of first frame
8. Holding-down section of first frame
9. Elbow
10. Second frame
11. Slide surface of second frame
12. Connection section of headgear strap in second frame
13. Connection section of headgear strap in second frame
14. Bearing
15. Connection section with elbow
16. Headgear
17. Left headgear strap
18. Right headgear strap

BEST MODE TO CARRY OUT THE INVENTION

The present invention is next described in detail.

As described above, the present invention is a respiratory mask system contacting the face of a user for supplying respiratory gas under positive pressure to the user and comprises a mask cushion covering a nose, a nose and a mouth or a full face, a first frame connected with the above mask cushion capable of supplying respiratory gas under positive pressure from a means for supplying respiratory gas under positive pressure, and a second frame connected with a headgear strap, in which the above mask cushion is disposed on a face side of the above first frame, the above first frame is disposed on a face side of the above second frame, a slide surface is formed on at least a side of the above first frame facing the above second frame or a side of the above second frame facing the above first frame, and the above first frame is connected slidably with the above second frame along the above slide surface.

A means for supplying respiratory gas under positive pressure herein is a means to transport positive pressure gas supplied from a respiratory equipment to a respiratory mask system and generally transports respiratory gas under positive pressure to the respiratory mask system by connecting the respiratory equipment with the respiratory mask system using a flexible hose or by possibly using a rigid tube or by directly connecting the respiratory equipment with the respiratory mask system. Such a supply means may use other mechanism so far as the respiratory gas under positive pressure may be transported to a respiratory mask system.

(Mask Cushion)

A mask cushion in a respiratory mask cushion of the present invention is a cushion to cover a nose, a nose and a mouth or a full face and formed in a hollow shape, that is, a roughly cylindrical shape for respiratory gas under positive pressure to pass. At least a contact section with a face in this mask cushion is constructed from an elastic body and, for example, in a nasal mask cushion, a structure or material capable of closely contacting a periphery of the nose of a user is used. Such construction allows absorbing individual difference in a facial shape of a user as well as preventing respiratory gas under positive pressure from leaking.

Such a structure capable of good sealing is known and, for example, includes a double membrane structure according to Patent Document 3 as a suitable example, but is not limited by this structure so far as seal is in a level not to allow leaking of respiratory gas under positive pressure in practical use. Materials for a face contact section of such a mask cushion include, for example, a silicone rubber.

For example, since air tightness of a respiratory gas under positive pressure in a nasal mask cushion is secured by pressing to a periphery of the nose of a user, a circumference of an open end at a user side is typically molded into substantially an isosceles triangular shape reflecting the nasal shape, for example, such as a structure according to Patent Document 3. A shape of a whole nasal mask cushion is suitably made substantially isosceles triangular reflecting a shape of an open end in a user side, but may be in other shape so far as air tightness is assured.

Sections other than a face contact section of a mask cushion are not necessarily constructed from an elastic body. Their intermediate sections may further have, for example, a bellow structure according to Patent Document 1.

A mask cushion may be molded in a single-piece, but may include a combination of a plurality of parts so far as leak of respiratory gas under positive pressure does not occur.

(First Frame)

A first frame in a respiratory mask system of the present invention comprises a connection with a mask cushion configured to enable supplying a respiratory gas under positive pressure from a means for supplying respiratory gas under positive pressure.

Such a first frame typically has a mask cushion fixed to its face side and a connection section with an elbow in its opposite side as well as a convex slide surface formed in a spherical shape and protruding in a direction opposite to the face side. And the first frame is connected with a second frame in a ball-joint like form through the slide surface, and the first frame is further provided with a holding-down section with a shape to prevent disengagement from the second frame.

As a typical example of such a first frame is specifically described, the first frame has, roughly speaking, a face on a face side and a face opposite to it. The mask cushion described above is fixed on the face side. On the other hand, a face on an opposite side to the face has a slide surface in a shape of a spherical surface and a holding-down section as well as a connection section with an elbow. "Fixing" of the mask cushion includes fixing by adhesion and fixing by a fixing member such as a clamp and the like, but also a case in which two or more parts among the first frame, mask cushion and elbow are molded in a single-piece. Conversely, the first frame is provided with the slide surface in a shape of a spherical surface and a holding-down section, and these sections may be molded in a single-piece, or manufactured separately and assembled later.

In a respiratory mask system of the present invention, a slide surface may be formed on at least a side of a first frame facing a second frame or a side of the second frame facing the first frame, but a slide surface in a shape of the spherical surface is preferably formed on a face in an opposite side to a face side of the first frame as the typical example described above. A spherical surface herein refers to a shape, of which a part of a surface of a sphere is cut out. And such a spherical surface is in a convex form protruding in a direction opposite to the face side. More preferably, the spherical surface has a shape, of which a part of the surface of a sphere is cut through a plane, that is, preferably a shape of a circular convex mirror as viewed from the front side of a user. Such a shape makes relative movement between the first frame and the second frame smoother, enabling to further reduce or absorb problematic lateral slip.

The center of a hypothetical sphere 19 forming the spherical surface is preferably positioned above or near the center of revolving movement of the head of a user from side to side and up and down. The center of the revolving movement is generally positioned above or near the center of such a spherical form provided that the head of a user is assumed roughly spherical. Such a configuration prevents the mask cushion from tilting against the face of a user, even if the user wearing the mask tilts his head from side to side and up and down.

A respiratory mask system of the present invention is used by connecting a means for supplying respiratory gas under positive pressure such as a hose and the like for supplying respiratory gas under positive pressure. Accordingly, a face of an opposite side to the face of a first frame is typically provided with a connection section with an elbow, which is a mounting section of a means for supplying respiratory gas under positive pressure. And the first frame has to be provided with a gas channel, through which respiratory gas under positive pressure introduced from a means for supplying respiratory gas under positive pressure may reach a mask cushion mounted on the first frame.

A first frame in a respiratory mask system of the present invention also has a role of connecting a mask cushion and an elbow and may also have a holding-down section or slide surface so that a strong material within a limit required to realize such functions is used. It is generally constructed from plastics, for example, polycarbonate.

As described above, a first frame in a respiratory mask system of the present invention is suitable to fix a mask cushion, capable of connecting a connection section of a means for supplying respiratory gas under positive pressure and capable of providing a holding-down section and a slide surface if needed and any one of structures may be used so far as the structure does not prevent relative displacement between the first frame and second frame.

(Second Frame)

A second frame in a respiratory mask system of the present invention is connected with a headgear strap and has a role to fix the mask system together with this headgear strap and a headgear on the face of a user. Accordingly, the second frame is provided with a mounting section for a headgear strap or molded with a headgear section in a single-piece. Any one of these shapes may be used so far as the mask system of the present invention may be fixed on a face.

As described above, in the respiratory mask system of the present invention, a slide surface is formed on at least a side of a first frame facing a second frame or a side of the second frame facing the first frame, and in particular, when the slide surface is provided on the face of an opposite side to a face side of the first frame, a slide surface corresponding to the slide surface of the first frame is preferably also provided on the face of a face side of the second frame. This gives a stable sliding state in relative displacement between the first frame and the second frame, enabling structurally good balance.

Furthermore, preferably a slide surface of a second frame is formed in a shape of a spherical surface and in a convex shape protruding in the direction opposite to a face side and the first frame is connected with the second frame in a ball-joint like form through this slide surface. More preferably, the spherical surface has a shape, of which a part of the surface of a sphere is cut through a plane, that is, preferably a shape of a circular concave mirror as viewed from the front side of a user. Such a shape makes relative movement between the first frame and the second frame smoother, enabling to further reduce or absorb problematic lateral slip.

In particular, a center of this spherical surface as a slide surface is preferably positioned above or near a center of revolving movement of the head of a user from side to side and up and down. In this case, a mask cushion does not tilt against the face of a user, even if the user tilts his head from side to side and up and down and pressure from the mask cushion on the face of a user is kept uniformly.

A first frame and a second frame not only must contact through the spherical slid surfaces each frame has, but also enable relative movement through the slide surface. A range of such movement may be in a level to dissolve the problematic slip. A specific numerical value depends on each shape of respiratory mask systems in the present invention, but those skilled in the art may easily determine a range to satisfy the movement after simple trials.

In a case of a construction, of which a second frame is positioned between a first frame and a holding-down section, a section having the slide surface as a part of such a second frame is preferably in a shape to concave a flat plate in a spherical shape. This section is sandwiched between a slide surface of the first frame and the holding-down section to prevent the first frame from coming off from the second frame. The reason for providing the holding-down section on the first frame is that, when tension is applied to a headgear strap or pressure of respiratory gas under positive pressure is applied, force is exerted in a direction to press a slide surface of the first frame on a slide surface of the second frame, but provision of the holding-down section on the first frame is required to prevent both from detaching, even if this is not the case.

Apart of a holding-down section of the first section contacting the second frame is preferably in a roughly spherical shape corresponding to a shape of the face opposite to a slide surface of such a second frame. A shape of the face opposite to a slide surface of the second frame or a holding-down section of the first frame section contacting the second frame may have other shape so far as it does not prevent relative movement between the first frame and the second frame along the slide surface but prevents the first frame from detaching the second frame.

A second frame has a role to fix a respiratory mask system on the face of a user and uses a strong material within a limit required thereto. It is generally constructed from plastics, for instance, polycarbonate.

(Elbow)

An elbow is connected with a first frame to mount a means for supplying respiratory gas under positive pressure such as a hose and the like for supplying respiratory gas under positive pressure. A structure of such an elbow may use a known mechanism so far as it has a structure to prevent respiratory gas under positive pressure from leaking at a connection section with a hose and the like. Such an elbow is preferably rotatably connected with a first frame. In the description of the present specification, it is expressed as "elbow" for convenience, but so-called "L-shaped" is not required so far as a means for supplying respiratory gas under positive pressure may be mounted, a channel for respiratory gas under positive pressure may be secured in its inside and it has a structure not preventing relative movement between the first frame and the second frame through the slide surface described above. However, an L-shape shown in Examples is preferred under consideration of easy handling after mounting a hose and the like for supplying respiratory gas under positive pressure. A means for supplying respiratory gas under positive pressure such as a hose and the like for supplying respiratory gas under positive pressure, in the first place, may also be directly mounted on the first frame without using the elbow.

(Preferred Positional Relationship of Each Section)

In a nasal respiratory mask system of the present invention, a mask cushion is positioned on a face side of a first frame and the first frame is positioned on a face side of a second frame. Furthermore, a slide surface of the first frame, a slide surface of the second frame facing it, other sections of the second frame, a headgear strap connected with it, an elbow and a holding-down section of the first frame are preferably disposed in the face opposite to the face side of the first frame. Each section and each member have to be further positioned not interfering slide movement, since the slide surface of the first frame and the slide surface of the second frame have to be allowed to slide movement in a certain range.

A connection section of the first frame with the elbow may be mounted on a different site from the slide surface of the first frame, but preferably provided with a hole on the slide surface of the first frame. In particular, the shape of the slide surface of the first frame is preferably a circular convex mirror shape as viewed from a front side of a user, and in this case, the connection section with the elbow is particularly preferred to fix at its center. In either case a through-hole is preferably provided at least on a site facing the contact section in the second frame in order not to prevent movement of the second frame including a headgear and a strap connected thereto. For example, when a connection section with an elbow is fixed on a center of the slide surface of the first frame with a circular convex mirror shape, a hole is necessarily formed also on the slide surface of the second frame. That is, the slide surface of the second frame becomes a doughnut shape. A size of the hole has to be not only in a range through which a section to fix the connection section with the elbow passes freely, but also not preventing the slide movement described above.

Figure 3:
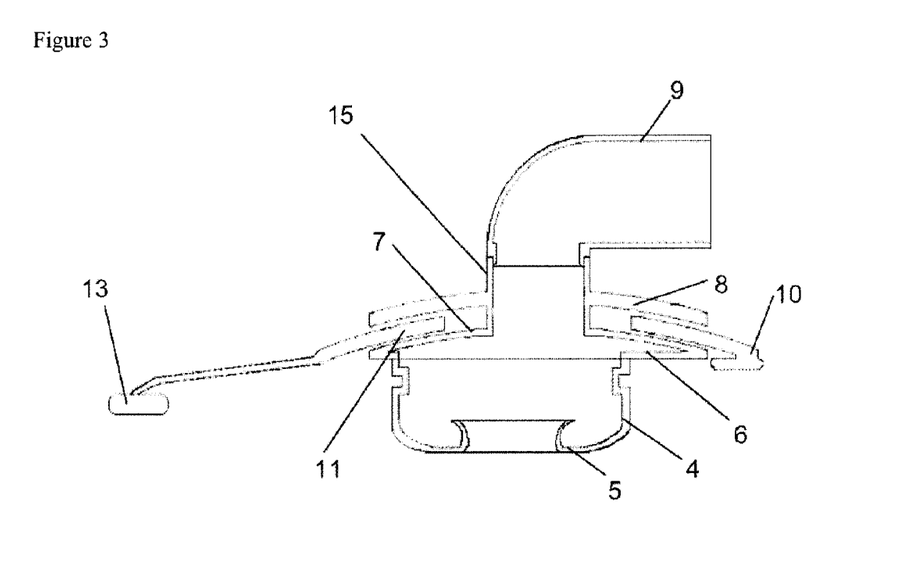
FIG. 3 is a sectional side view of a nasal respiratory mask system in reference to Example 1 of the present invention.

Further, a second frame is preferably constructed with a holding-down section in a first frame section to prevent disengagement. Such a holding-down section provided may be positioned at a location to hold down any section of the second frame so far as its objective is achieved, but preferably has a structure to hold down a slide surface section of the second frame. For example, a structure to hold down from a periphery of the slide surface section of the second frame may be used, but when a connection section with an elbow is mounted on a center of the slide surface in the first frame with a circular convex mirror shape as described above, a holding-down section is preferably mounted so as to extend outwards from a fixing section of an elbow in the connection section. A nasal respiratory mask system of the present invention shown in FIG. 3 is one of such examples. A holding-down section of the first frame in FIG. 3 is in a doughnut shape, but may be in a plurality of nail-shaped members so far as its objective is achieved. The same is true in case to hold down the second frame from periphery.

Figure 5:
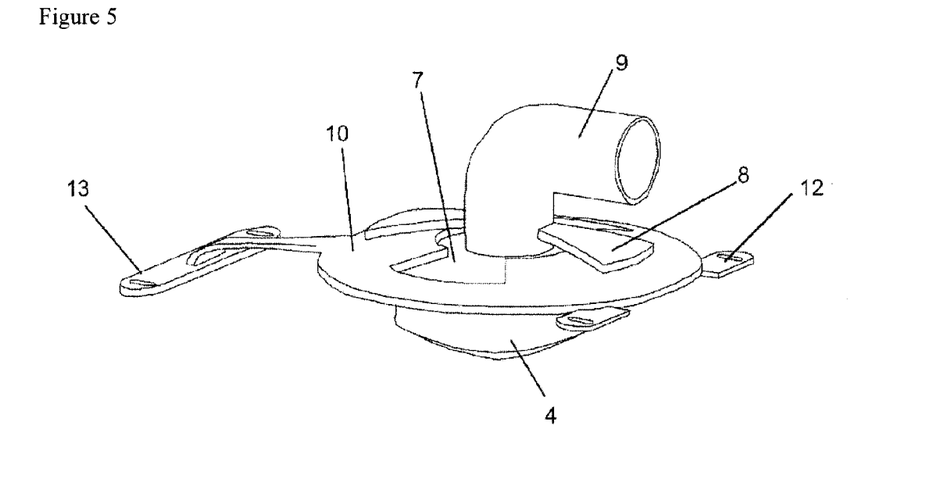
FIG. 5 is a perspective view of a respiratory mask system in reference to Example 2 of the present invention.

A structure shown in FIG. 3 is a preferred one, but at the same time may have such problems as difficulty in single-piece molding of a first frame, an elbow and a holding-down section and assembling parts after molding. Since a holding-down section of the first frame may have a shape to hold down only a part of the slide surface in the second frame, so far as preventing the first frame from detaching the second frame, a shape of a holding-down section of the first frame matches with a deleted section of a slide surface in the second frame as shown in FIG. 5 to enable inserting the second frame into the first frame, which is molded with the elbow in a single-piece.

An example of a preferred embodiment includes one further having a bearing on a slide surface between the first frame and the second frame. This is added to improve sliding. Such a bearing may be mounted on any side of the sliding surfaces. Additionally, a self-lubricating resin may be used or a lubricant such as grease and the like may be applied in order to improve slide movement.

EXAMPLE

Specific examples of the present invention are further described in detail in reference with drawings as follows.

Example 1

Figure 4:
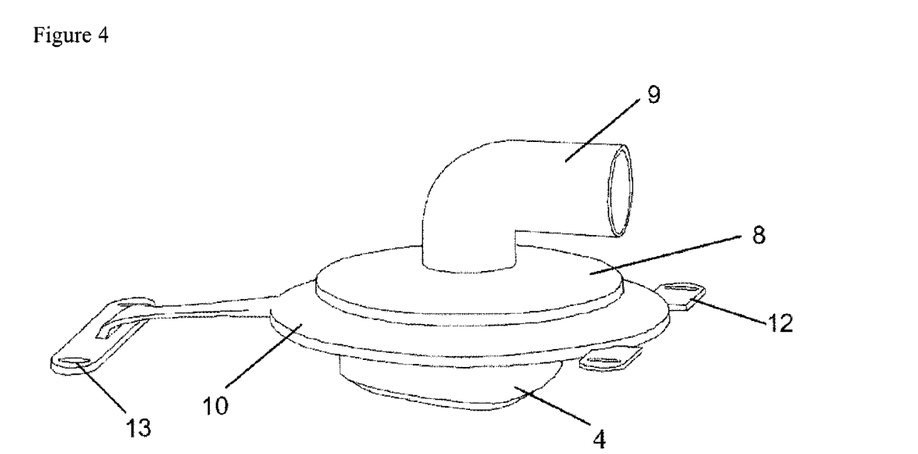
FIG. 4 is a perspective view of a nasal respiratory mask system in reference to above Example 1.

FIG. 3 demonstrates a sectional side view of a nasal respiratory mask system as an example of the present invention. FIG. 4 demonstrates a perspective view of this nasal respiratory mask system. A mask cushion 4 (nasal mask cushion herein) is fixed on the face side of a first frame 6. On the other hand, a slide surface 7 is mounted on an opposite side to the face of the first frame 6. A shape of the slide surface 7 section of this first frame is roughly circular convex mirror shape with a hole at the center section, on which a roughly cylindrical connection section 15 to connect an elbow 9 with the first frame 6 is mounted. An inside of the first frame 6 is communicated with an inside of the elbow 9 via this connection section 15. A holding-down section 8 having a circular convex mirror shape and perforated at a central part is fixed on an intermediate section of such connection section 15.

A second frame 10 is positioned between a slide surface 7 and a holding-down section 8 in the first frame and a slide surface 11 with a roughly circular convex mirror shape and perforated at the central part is mounted on the side of this second frame 10 facing the slide surface 7 of the first frame. The first frame 6 and the second frame 10 are connected in a ball-joint like form through this slide surface 11 and the slide surface 7 of the first frame. A holding-down section 8 of the first frame 6 prevents the first frame 6 from detaching the second frame 10. The second frame 10 is mounted with two connection sections 12 for a headgear strap positioned on the mouth side of a user and two connection sections 13 for a headgear strap positioned on the forehead side of a user.

In such a nasal respiratory mask system, respiratory gas under positive pressure introduced from a hose for supplying respiratory gas under positive pressure passes through an elbow 9, a connection section 15, an inside of a first frame 6 and holes provided thereto (not shown) to reach an inside of a nasal mask cushion 4.

Example 2

FIG. 5 demonstrates a perspective view of an example of a respiratory mask system in the present invention. This is basically similar to a nasal respiratory mask system according to Example 1 and providing a pair of holding-down sections 8 of a first frame in a fan-like form as well as providing a slit to match its shape on a slide surface 11 section of the second frame allows for single-piece molding of a first frame 6 and a connection section 15 with an elbow 9 and then assembling a second frame 10 with this piece.

Figure 6:
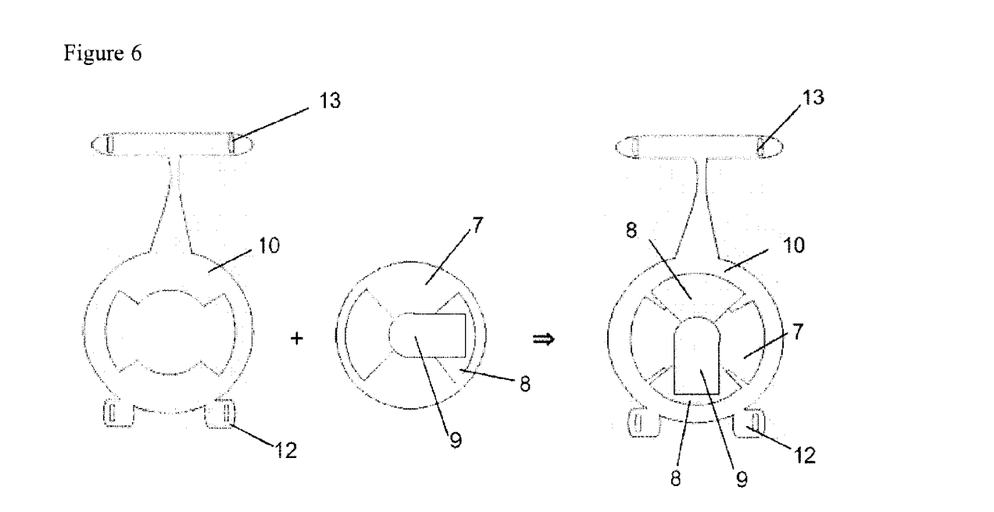
FIG. 6 is a diagram to illustrate a method to assemble a respiratory mask system in reference to above Example 2.

FIG. 6 demonstrates a method to assemble such a respiratory mask system. After a holding-down section 8 of the first frame 6 is turned by 90 degrees against the second frame 10 to insert, the holding-down section 8 is turned by 90 degrees in an opposite direction to assemble.

Example 3

Figure 7:
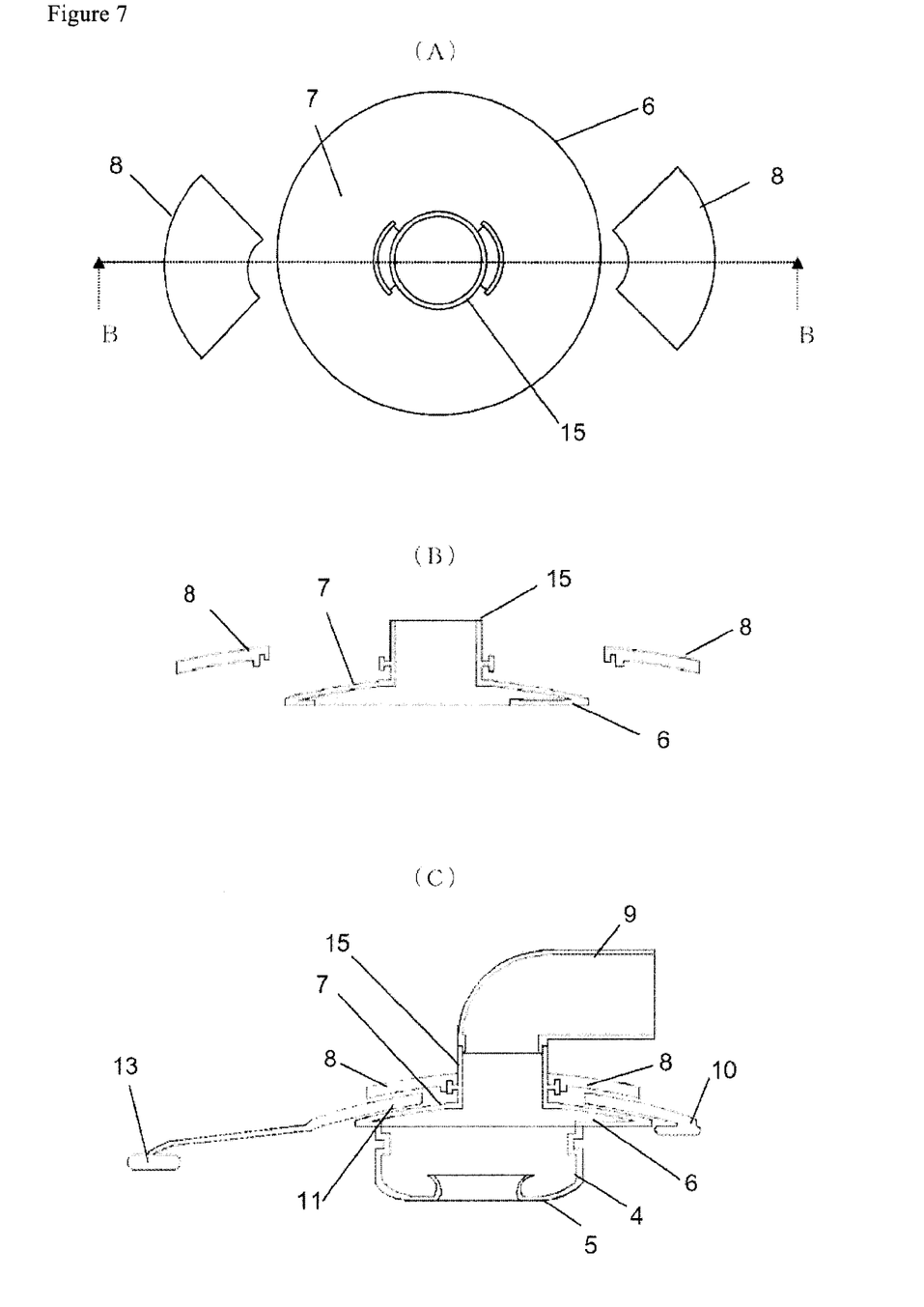
FIG. 7 is a diagram to illustrate a method to assemble a respiratory mask system in reference to Example 3 of the present invention.

FIG. 7 demonstrates a respiratory mask system as a modified example of Example 2. The present respiratory mask system has a structure, in which a pair of holding-down sections 8 in fan-like shape is detachably mounted on a connection section 15 of the first frame 6. FIG. 7(A) herein is a plain view showing only the first frame 6 and the holding-down section 8, FIG. 7(B) is a sectional side view along a B-B-line in FIG. 7(A) and FIG. 7(C) is a sectional side view to demonstrate an assembled state of a whole respiratory mask system. A method to assemble the present respiratory mask system is, by making the holding-down section 8 of the first frame as a separate part from other section of the first frame, it is engaged, after a connection section 15 in a first frame 6 and an elbow 9 fixed thereto are inserted into a hole at a center of a slide surface 11 of the second frame, with an engaging section mounted on a periphery of the connection section 15 completing assembling.

Example 4

Figure 8:
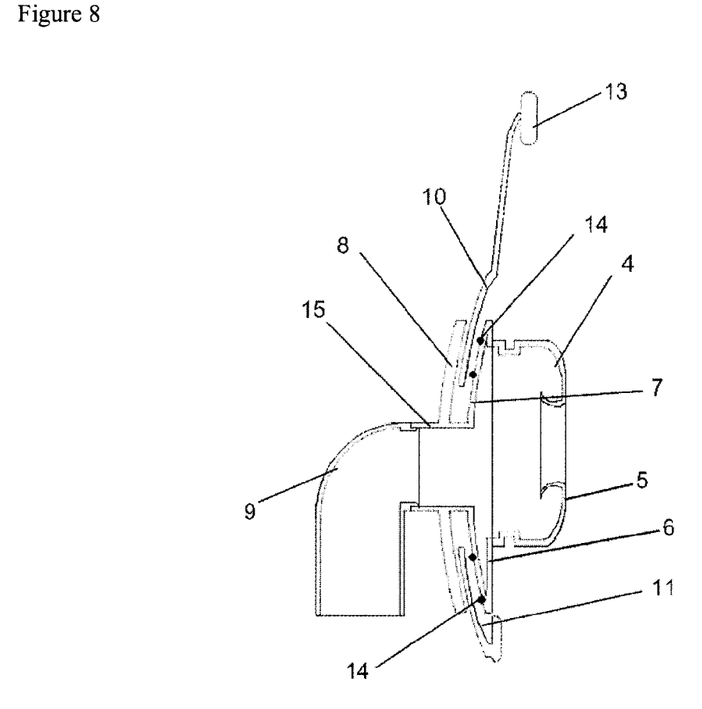
FIG. 8 is a sectional side view of a respiratory mask system in reference to Example 4 of the present invention.

FIG. 8 demonstrates a sectional side view of an example of a respiratory mask system in the present invention. The present respiratory mask system is basically similar to the nasal respiratory mask system according to Example 1, but has a bearing 14 provided between a slide surface 7 of the first frame and a slide surface 11 of the second frame in order to improve slide motion. Bearing 14 herein is provided on the slide surface 7 side of the first frame.

Example 5

Figure 9:
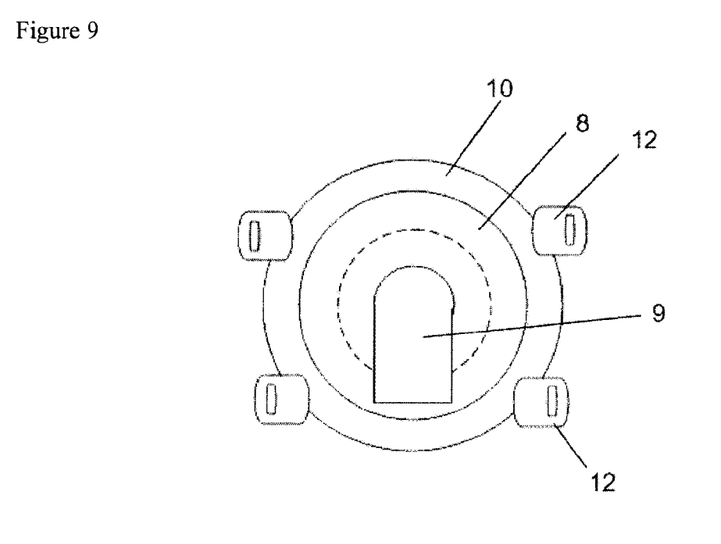
FIG. 9 is a front view of a respiratory mask system in reference to Example 5 of the present invention.

FIG. 9 demonstrates a plain view of an example of a respiratory mask system in the present invention. The present respiratory mask system is basically similar to the nasal respiratory mask system according to Example 1, but is provided with four connection sections 12 for a headgear strap on the second frame 10 similar as connection sections 12 for a headgear strap on a mouth side as shown in FIG. 3, instead of mounting connection sections 13 for a headgear strap on a forehead side as shown in FIG. 3.

INDUSTRIAL APPLICABILITY

The present invention provides a respiratory mask system used in CPAP therapy or NIPPV therapy.

The invention claimed is:

1. A respiratory mask system, contacting the face of a user for supplying respiratory gas under positive pressure to the user, comprising:
    a mask cushion covering a nose, a nose and a mouth or a full face;
    a first frame connected with the mask cushion enabling to supply respiratory gas under positive pressure from a means for supplying respiratory gas under positive pressure; and
    a second frame connected with a headgear strap,
    the mask cushion being disposed on the face side of the first frame and the first frame being disposed on the face side of the second frame,
    a pair of slide surfaces being correspondingly formed in the side of the first frame facing the second frame and in the side of the second frame facing the first frame, and the first frame being connected slidably with the second frame along the slide surface, and the first frame and the second frame being relatively rotatable in any direction by 360° along the pair of slide surfaces, wherein a holding-down section is provided to prevent detachment of connection between the first frame and the second frame, even if tension is not applied to a headgear strap or pressure of respiratory gas under positive pressure is not applied, the provision of the holding-down section preventing the both first and second frames from detaching, wherein at least one slide surface of the pair of slide surfaces is formed along a portion of a hypothetical sphere, having a center, the slide surface having a spherical surface and a convex shape protruding in the direction opposite to the face side, and the first frame is connected with the second frame in a ball-joint like form through the slide surface, and wherein center of a revolving movement of a user's head from side to side and up and down is positioned on or near the center of the hypothetical sphere.

2. The respiratory mask system according to claim 1, wherein a connection section with an elbow as a mounting section of a means for supplying respiratory gas under positive pressure is provided in a position corresponding to a center of the slide surface in the first frame and a through-hole is provided at least at a site facing the connection section in the second frame.

3. The respiratory mask system according to claim 1, wherein a bearing is further provided on at least a slide surface of the first frame or a slide surface of the second surface.

4. The respiratory mask system according to claim 1, wherein the holding-down section is provided in the first frame, and a shape of the holding-down section of the first frame matches with a deleted section of the slide surface in the second frame.

5. The respiratory mask system according to claim 1, wherein the holding-down section is detachably mounted on the first frame.

6. A respiratory mask system, contacting the face of a user for supplying respiratory gas under positive pressure to the user, comprising:

a mask cushion covering a nose, a nose and a mouth or a full face;

a first frame connected with the mask cushion enabling to supply respiratory gas under positive pressure from a means for supplying respiratory gas under positive pressure; and a second frame connected with a headgear strap, the mask cushion being disposed on the side of the first frame and the first frame being disposed on the face side of the second frame, a pair of slide surfaces being correspondingly formed in the side of the first frame facing the second frame and in the side of the second frame facing the first frame, and the first frame being connected slidably with the second frame along the slide surface, wherein a holding-down section is provided to prevent detachment of connection between the first frame and the second frame, the slide surface of the second frame being sandwiched between a slide surface of the first frame and the holding-down section, wherein at least one slide surface of the pair of slide surfaces is formed along a portion of a hypothetical sphere, having a center, the slide surface having a spherical surface and in a convex shape protruding in the direction opposite to the face side, and the first frame is connected with the second frame in a ball-joint like form through the slide surface, and wherein a center of a revolving movement of a user's head from side to side and up and down is positioned on or near the center of the hypothetical sphere.

7. The respiratory mask system according to claim 6, wherein the holding-down section is provided in the first frame, and a shape of the holding-down section of the first frame matches with a deleted section of the slide surface in the second frame.

8. The respiratory mask system according to claim 6, wherein the holding-down section is detachably mounted on the first frame.

* * * * *